US008357163B2

(12) United States Patent
Sidebotham et al.

(10) Patent No.: US 8,357,163 B2
(45) Date of Patent: Jan. 22, 2013

(54) LOW COST MODULAR TAPERED AND SPHERICAL HOLLOW REAMERS FOR MEDICAL APPLICATIONS

(76) Inventors: Christopher G. Sidebotham, Mendham, NJ (US); Randall J. Lewis, Bethesda, MD (US)

( * ) Notice: Subject to any disclaimer, the term of this patent is extended or adjusted under 35 U.S.C. 154(b) by 673 days.

(21) Appl. No.: 12/583,691

(22) Filed: Aug. 24, 2009

(65) Prior Publication Data

US 2010/0063507 A1    Mar. 11, 2010

Related U.S. Application Data

(63) Continuation-in-part of application No. 11/704,754, filed on Feb. 9, 2007.

(51) Int. Cl.
*A61B 17/00* (2006.01)
(52) U.S. Cl. .......................................................... 606/80
(58) Field of Classification Search .................. 606/80
See application file for complete search history.

(56) References Cited

U.S. PATENT DOCUMENTS

| | | | |
|---|---|---|---|
| 4,116,200 A | 9/1978 | Braun et al. ..................... 605/81 |
| 4,473,070 A * | 9/1984 | Matthews et al. ............... 606/80 |
| 4,811,632 A | 3/1989 | Salyer ............................. 76/115 |
| 5,100,267 A | 3/1992 | Salyer ............................. 407/54 |
| 5,116,165 A | 5/1992 | Salyer ............................. 407/54 |
| 5,171,312 A | 12/1992 | Salyer ............................ 606/81 |
| 5,171,313 A | 12/1992 | Salyer ............................ 606/86 |
| 5,190,548 A | 3/1993 | Davis ............................. 606/80 |
| 5,236,433 A | 8/1993 | Salyer ............................ 606/91 |
| 5,282,804 A | 2/1994 | Salyer ............................ 606/86 |
| 5,299,893 A | 4/1994 | Salyer ............................ 407/54 |
| 5,376,092 A | 12/1994 | Hein et al. ...................... 606/81 |
| 5,501,686 A | 3/1996 | Salyer ............................ 696/79 |
| 5,549,613 A | 8/1996 | Goble et al. .................... 606/80 |
| 5,556,399 A | 9/1996 | Huebner ......................... 606/80 |
| 5,690,634 A | 11/1997 | Muller et al. ................... 606/80 |
| 5,709,688 A | 1/1998 | Salyer ............................ 606/81 |

(Continued)

FOREIGN PATENT DOCUMENTS

WO        WO/9007908        7/1990

OTHER PUBLICATIONS

"Effect of Flexible Drive Diameter and Reamer Design on the Increase of Pressure in the Medullary Cavity During reaming", Mueller et al., PubMed (1993) http://www.ncbi.nlm.nih.gov/entrez/query.fcgi?db=pubmed&cmd=Retrieve&dopt=Abstract_Plus&list_uids=8168875&query_hl=2&itool=pubmed_Brief.

(Continued)

*Primary Examiner* — Nicholas Woodall
(74) *Attorney, Agent, or Firm* — Ernest D. Buff; Ernest D. Buff & Assoc. LLC; Margaret A. LaCroix, Esq.

(57) ABSTRACT

An easy-to-assemble modular tapered or spherical reamer for medical applications includes a shaft portion, a disposable tapered or spherical hollow reamer and a guide pin. The shaft proximal end attaches to a drill and the distal end has a tapered body element with a tapered external surface and a central aperture. The disposable tapered or spherical hollow reamer has a central aperture that accepts the guide pin and an interior taper that matches the taper of the tapered body element. The guide pin has attachment means to attach its distal end to the central aperture in the reamer, and the proximal end to the central aperture of the tapered body element of the shaft, assuring reamer/shaft concentricity. Contact between the reamer taper and the taper of the tapered body element aids this concentricity. Torque transmission between the shaft and the reamer is accomplished by torque transmitting tabs or a threaded connection.

11 Claims, 10 Drawing Sheets

U.S. PATENT DOCUMENTS

| | | | |
|---|---|---|---|
| 5,755,719 A | 5/1998 | Frieze | 606/81 |
| 5,817,096 A | 10/1998 | Salyer | 606/81 |
| 5,908,423 A * | 6/1999 | Kashuba et al. | 606/80 |
| 5,954,671 A | 9/1999 | O'Neill | 600/567 |
| 5,976,144 A | 11/1999 | Fishbein et al. | 606/80 |
| 5,980,170 A | 11/1999 | Salyer | 408/239 R |
| 6,001,105 A | 12/1999 | Salyer | 606/81 |
| 6,015,411 A * | 1/2000 | Ohkoshi et al. | 606/80 |
| 6,168,600 B1 | 1/2001 | Grace et al. | 606/81 |
| 6,193,722 B1 | 2/2001 | Zech et al. | 606/79 |
| 6,332,886 B1 | 12/2001 | Green et al. | 608/80 |
| 6,409,732 B1 | 6/2002 | Salyer | 606/81 |
| 6,428,543 B1 | 8/2002 | Salyer | 606/81 |
| 6,451,023 B1 | 9/2002 | Salazar et al. | 606/86 |
| 6,517,581 B2 * | 2/2003 | Blamey | 623/22.12 |
| 6,730,094 B2 | 5/2004 | Salyer et al. | 606/80 |
| 6,875,217 B2 | 4/2005 | Wolford | 606/81 |
| 6,890,336 B2 * | 5/2005 | Nordman | 606/80 |
| 7,074,224 B2 | 7/2006 | Daniels et al. | 606/80 |
| 2003/0181916 A1 | 9/2003 | Wolfdord | 606/81 |
| 2005/0113836 A1 | 5/2005 | Lozier et al. | 606/80 |
| 2006/0004371 A1 | 1/2006 | Williams et al. | 606/80 |
| 2006/0095041 A1 | 5/2006 | Fehlbaum et al. | 606/81 |
| 2006/0184174 A1 | 8/2006 | Harris et al. | 606/80 |
| 2006/0235539 A1 | 10/2006 | Blunn et al. | 623/22.12 |
| 2006/0264956 A1 | 11/2006 | Orbay et al. | 606/80 |
| 2008/0195104 A1 * | 8/2008 | Sidebotham et al. | 606/80 |
| 2011/0015634 A1 * | 1/2011 | Smith et al. | 606/80 |

OTHER PUBLICATIONS

"Single Use Sterile Power Equipment", Orthomedix.com, at http://www.orthomedex.com/index.html.

* cited by examiner

Prior Art

LOW COST MODULAR TAPERED AND SPHERICAL HOLLOW REAMERS FOR MEDICAL APPLICATIONS

This is a Continuation-In-Part of application Serial No. U.S. Ser. No. 11/704,754, Filed Feb. 9, 2007 for "Hollow Reamer For Medical Applications", the disclosure of which is hereby incorporated in its entirety by reference thereto.

BACKGROUND OF THE INVENTION

1. Field of the Invention

The present invention relates to a modular easily assembled tapered or spherical hollow reamer for medical applications having a disposable cutter that includes one or more bone debris capturing cavities; and more particularly, to a hollow tapered or spherical reamer having a disposable reamer assembly, which can be attached or detached to a reusable shaft portion using a special tool, wherein the assembly is aided by a guide pin.

2. Description of the Prior Art

Reaming of the internal canal of bones is required in many surgical procedures of orthopedic surgery. Such procedures include hip replacement, knee replacement and shoulder replacement. Reamers are also used in procedures that involve the internal fixation of fractures. Prior art reamers for reaming internal canal in bones typically use a rigid or a flexible shaft. Typically, reaming of the internal bone canal is achieved through utilization of a solid cylindrical or tapered reamer. Solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid cylindrical or tapered reamers are intended for multiple uses and therefore become less efficient after each surgery, resulting in poor cutting performance and bone necrosis. Dull blades also incorporate bone debris or bone cement debris into the living bone tissue, creating bone healing problems. Similar problems are also encountered in reaming a spherical cavity for the attachment of an acetabular cup.

U.S. Pat. No. 4,116,200 to Braun et al. discloses a milling tool for surgical purposes. The surgical milling tool is a hand-operated milling machine for milling the heads or sockets of bone joints and has a spherical shape. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup. The hemispherical shape of the cup provides the ability to hollow out the arcuate shape of the bone joints. Bone and cartilage shavings are formed during the milling process and are collected in a border area inside of the hemispherical cup. The surgical milling tool is provided for multiple uses and therefore the tool tends to become less efficient after each surgery, resulting in poor cutting performance and bone necrosis. Moreover, the spherically shaped reaming tool is not tapered.

U.S. Pat. No. 5,190,548 to Davis discloses a surgical reamer. This surgical bone reamer includes a rotatable, elongated shank having a proximal end, a distal end and a longitudinal axis. A reaming head mounted on the distal end. A plurality of equally spaced walls is radially disposed on the reaming head around the longitudinal axis. Tip edges for penetrating bone are defined on the radial walls to be disposed angularly with the longitudinal axis. Reaming edges joined to the tip edges extend longitudinally from the tip edges in the proximal direction parallel to and an equal radial distance from the longitudinal axis for reaming a cylindrical tunnel when the reaming head is rotated in bone. Tapered flutes disposed angularly between the tip edges and the radial walls permit bone to be evacuated through the reaming head when forming a tunnel in bone. The reaming head is provided with angular tips and edges for penetrating the bone and is thus not a single use disposable cutter. The debris created is not stored away from the cutting edge and thus previously cut material may be included in the bone.

U.S. Pat. No. 5,549,613 to Goble et al. discloses a modular surgical drill. This modular surgical drill is in the form of a rigid drill shaft and a drill bit, which are connected together by a tongue-and-groove arrangement attaching the rear end of the drill bit to the forward end of the drill shaft. Each of the shaft and drill bit are provided with through bores extending centrally through their entire length. These bores become aligned upon assembly of the drill bit and shaft. The modular drill is intended to be employed with a guidewire for drilling holes into bone. The assembled drill bit and shaft are placed on the guidewire and moved down such guidewire into contact with the bone, whereupon a tunnel may be formed into the bone by rotating and advancing the drill bit along the guidewire. The dimensions of the bore and guidewire are so selected as to prevent the drill bit and drill shaft from moving relative to one another once they are assembled and mounted on the guidewire. Debris created during drilling is not removed and collected away from the cutting location. The central bore is solid and as such does not receive cut bone debris. The cutter used is not disposable.

U.S. Pat. No. 5,556,399 to Huebner discloses a bone-harvesting drill apparatus and method for its use. A coring drill harvests bone from a donor area of the human body. The drill bit is formed with a cylindrical, hollow shaft and a half-conical tip or cutting head. The cutting head is provided with a sharpened edge, which meets at an apex with a non-sharpened edge, forming an obtuse angle of approximately 120 degrees. The sharpened edge is configured to cut into bone when the drill bit is rotated in a clockwise direction. With the apex directed against a section of bone, the cutting edge sheers off fragments of bone, which are then drawn upwardly through the hollow shank of the drill bit. As the drill bit is forced downwardly, continuous cutting action occurs and the morselized bone can then be removed from the shank and used to build-up bone in other areas to which it is transplanted. The drill bit fittingly mates on the distal end a fitting that renders the drill bit physically compatible with a conventional chuck. The bit includes a pair of diametrically opposed, oppositely inclined recesses that cooperate with a crossbar member within a bit-receiving bore of the fitting. When the aligned drill bit is pressed into the fitting, the crossbar member cams along the inclined recesses causing the bit to rotate relative to the fitting. The resulting frictional engagement between the recesses and the crossbar member, along with a detent assembly between the bit and the fitting, securely lock the bit onto the distal end of the fitting, yet render removal possible by the use of a removal tool. The bone harvesting tool provides a non-disposable cutter. Reuse of the cutter dulls the beveled lip edges. Moreover, the harvested bone collection central bore requires a thorough cleaning prior to each use, creating contamination possibilities.

U.S. Pat. No. 5,690,634 to Muller et al. discloses a medullary drill head. This drill head for intramedullary drilling has a front part, a middle part and a rear part and is shaped as a hollow body of revolution. The front and rear parts have spiral slots formed with cutting edges. The rear part has an attachment for coupling to a drilling shaft. The drill head is not disposable, and as a result, the drill head is continuously reused, resulting in dulling of the cutting edges. Moreover, the drill head includes three openings in the form of spirally shaped slots configured to have cutting edges similar to a grater; and has no place to collect bone debris.

U.S. Pat. No. 5,954,671 to O'Neill discloses a bone harvesting method and apparatus. This apparatus and method harvests bone using a manual, cylindrical, multi-directional coring device with a guided delivery system that can be inserted through a percutaneous or closed approach to extract precisely measured amounts of bone or bone marrow. A series of guide wires, obturators, dilators and cannulas are used as the exposure and delivery instrumentation for a cutting tool. The cutting tool has a tip with six cutting edges for cutting in all directions. This apparatus is a manual, cylindrical, multi-directional coring device with a guided delivery system to extract precisely measured amounts of bone or bone marrow. The cutter portion of the device is not disposable and is subject to wear and dull edges. This coring device does not suggest a tapered reamer.

U.S. Pat. No. 5,976,144 to Fishbein et al. discloses a hollow dome reamer with removable teeth. This surgical reamer has a hollow dome with apertures spaced apart arranged in arcs extending from an apex of the dome to the base portion of the dome, and removable teeth positioned in the apertures. Each cutting tooth has (i) a flange that is aligned flush with the external surface of the dome, (ii) a raised cutting edge extending above the flange and the external surface of the dome, and (iii) an interior passageway communicating between the outside and inside of the dome. A base plate may be removably secured on the base portion of the dome to provide closure for the central cavity of the dome. Although the teeth are removable, they are not disposable in nature; the teeth are removed for replacement or for re-sharpening and are used again. Removal of the small teeth may be cumbersome and difficult, and may even pose a danger during removal as the person removing the teeth may be cut by the sharp edges; replacement of the teeth into the apertures of the reamer will likely pose the same problems. The bone debris is not collected away from the cutting edges of the teeth. This hollow domed reamer has a spherical shape; does not suggest a tapered reamer.

U.S. Pat. No. 5,980,170 to Salyer discloses a tool driver. This tool driver has a shaft with a longitudinal axis and opposite ends. A boss is secured at one of the shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar containing the same dimensions as the groove in the boss of the tool driver. The bar thus fills and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The cutters are connected to the tip of the shaft and are spherical in nature for joint and patella reaming. In addition, the reamer cups are not disposable in nature. The bone fragments are not collected and kept away from the cutting edge. This spherically shaped reamer is not tapered.

U.S. Pat. No. 6,193,722 to Zech et al. discloses a hollow milling tool. The hollow milling tool produces substantially hollow cylindrical depressions in human or animal tissue. It also produces tissue pillars, which are removed at a harvest location, transported to a defect location and implanted. The hollow milling tool has teeth for the ablation of tissue which are arranged at the distal end of the milling tool at the end side. Furthermore, the milling tool has passages for transporting a cooling fluid to a cooling region of the milling tool lying near the distal end during the ablation of tissue. Teeth are constructed within the milling tool for accomplishing the depressions. These teeth will eventually need sharpening as the tool is used over time. No structure is contained within the '722 patent that discloses or suggests a tapered reamer.

U.S. Pat. No. 6,332,886 to Green et al. discloses a surgical reamer and method of using same. This device is used for expedited reaming of a medullary canal. The device includes a reamer head connected at the distal end of a rotatable drive shaft. The reamer head has a cutting head with five blades and flutes therebetween. Each blade has a front cutting portion. The blades can also include a side cutting portion. The method for removing material from the medullary canal of a bone includes the steps of reaming an area of the medullary canal to remove material; irrigating the material to be removed while reaming to reduce generation of heat and move removed material from the reaming area; and aspirating the removed material while reaming to create a negative intramedullary canal pressure to assist in the removal of the material. The blades and flutes at the reamer are reused and are subject to dulling. The bone chips are to be removed by the irrigating fluid, which means they are always present adjacent to the cutting portions and may be forced into the bone tissue. No disclosure in the '886 patent suggests a tapered reamer.

U.S. Pat. No. 6,451,023 to Salazar et al. discloses a guide bushing for a coring reamer, storage package for reamer assembly, and method of use. This guide bushing for a coring reamer has a tapered member with its largest diameter at its first end so that the guide bushing frictionally engages an internal surface of the reamer with a line contact. The guide bushing has a passage sized to slidably receive a guide pin. In use, the bushing advances in the proximal direction within the coring reamer along a guide pin while the excavated bone enters the passageway through the reamer. A storage package specifically designed for the reamer assembly is employed to remove the excavated bone from within the reamer. The package has a closed distal end and an open proximal end closeable with a cap. With the coring reamer received in cantilevered fashion through a central opening of the cap of the tube, and with an adapter that couples the coring reamer to a handpiece installed, a wrench is placed over the adapter and turned while the user grips peripheral surfaces of the cap to prevent rotation of the coring reamer. A plunger is inserted through the opening and through the coring reamer from the proximal end. The plunger is pushed through the reamer until the bone core and bushing fall out of the distal end of the coring reamer. The guide bushing for a coring reamer is appointed with an open end surrounded by peripheral teeth. The teeth are arranged peripheral to the body of the tube of the reamer. The tube is hollow and therefore excavated bone accumulates therewithin. The reamer, bushing and packaging are disposed of after use. The '023 patent discloses a bone excavating tool that does not prepare the bone canal for implantation of femoral implants. No structure is disclosed therein that suggests a tapered reamer.

U.S. Pat. No. 7,074,224 to Daniels et al. discloses a modular tapered reamer for bone preparation and associated method. This kit is for use in performing joint arthroplasty and includes a trial and a reamer. The reamer is said to be useful when preparing a cavity in the intramedullary canal of a long bone with the use of a driver, and to assist in performing a trial reduction. The reamer includes a first portion for placement at least partially in the cavity of the long bone and a second portion operably connected to the first portion. The reamer is removably connected to the driver to rotate the reamer. The trial is removably attachable to the reamer. This tapered reamer is not disposable and does not have provision for accumulating bone debris away from the cutting portion of the bone.

U.S. Patent Application Publication No. 2005/0113836 to Lozier et al. discloses an expandable reamer. This expandable reamer includes a cannulated shaft and a plurality of straight cutting blades having deformable points. The blades are hingably outwardly rotatable at the deformation points between a contracted position and an expanded position. In the contracted position, the blades are substantially parallel to the longitudinal axis of the cannulated shaft and, in the expanded position, the blades have at least a portion oriented radially outward from the longitudinal axis, thereby forming a larger diameter cutting surface in the expanded position and in the contracted position. The blades are formed from a portion of the cannulated shaft by, e.g. milling longitudinally extending slots through the wall of the cannulated shaft. The slots serve as flutes dividing the cutting edge and trailing edge of each adjacent blade. Each blade may also include more than one segment arranged along its length, the segments being coupled by deformation points. The expandable reamer may be used for cutting a cavity in a bone or other structure that is larger than the diameter of the entry point into the bone and greater than the diameter of the contracted reamer. The expandable reamer is not disposable. Since the expandable blades are deformably attached to the cannulated shaft, the cut bone debris is not collected away from the bone cutting region. As a result, fragments of cut bone debris may be pushed into the bone tissue by the deformable rotating blades.

U.S. Patent Application Publication No. 2006/0004371 to Williams et al. discloses an orthopedic reamer. This orthopedic reamer is for use in creating and sizing canals in a bone. The orthopedic reamer includes a non-polymeric cutting portion having at least one cutting surface thereon and a polymeric body portion covering at least a portion of the cutting portion. The at least one cutting surface is not covered by the polymeric body portion. The orthopedic reamer provides cutting components including a blade or saw like construction, rather than the plurality of teeth. Although the orthopedic reamer is appointed for disposability, the publication requires that the entire reamer, and not just the cutting portion, be disposed of. That is to say, the entire reamer, including the non-polymeric cutting portion and the polymeric body portion of the device are all disposed of; not just the cutter.

There remains a need in the art for a low cost modular easily assembled hollow tapered or spherical reamer for medical applications having a disposable hollow cutter assembly. Also needed in the art is a disposable hollow cutter assembly of the type described, which can be attached to a reusable shaft portion that provides means for reaming of the internal canal of bones or hemi-spherical bone cavities. Further needed in the art is a cutter assembly having means for collecting bone debris, thereby reducing heat build up by friction effects at the bone-cutter interface and keeping the collected debris displaced from the cutting edges, so that after one use of the reamer a new hollow cutter assembly can be utilized and the old hollow cutter assembly can be discarded.

SUMMARY OF THE INVENTION

The present invention provides a low cost, modular, easily assembled hollow tapered or spherical reamer that has a space for bone debris collection for medical applications and has a disposable cutter assembly. The cutter assembly is attached to a reusable shaft portion assisted by a guide pin using a special attachment tool.

The first group of embodiments of the invention relates to the attachment of a tapered hollow reamer to a reusable shaft using a special tool to precisely align the centerline of the shaft with that of the tapered hollow reamer assisted by a guide pin. The hollow reamer has its distal end permanently connected to a pilot provided with a central aperture for the insertion of guide pin during assembly. This central aperture may also be used to guide the reamer in a desired reaming direction by using a guide pin that is inserted into a bone cavity. The proximal other end of the reamer has a tapered interior that matches the taper provided on a external surface of a tapered body element provided on the distal end of the reusable shaft. Thus, when the reusable shaft is inserted and advanced into the reamer during assembly aided by the guide pin, the guide pin centers the reamer with respect to the center line of the shaft while the taper on the external surface of the tapered body element of the shaft engages the interior taper of the reamer, further assuring concentricity of alignment between the shaft and the reamer.

In a first variant of the first embodiment, the guide pin is barbell shaped. It connects the tapered hollow reamer pilot to the reusable shaft and is left within the reamer assembly, providing additional strength to the assembled hollow tapered reamer. This left-behind guide pin provides additional flexural strength to the reamer and thus is ideally suited for use in reaming the bone canal in a previously undrilled bone or a non-cannulated application. The torque transmission between the shaft and the reamer is accomplished through one or more torque transmission tabs in the tapered interior of the proximal end of the reamer, engaging with one or more slots present in the tapered body element of the shaft.

In a second variant of the first embodiment, a cylindrical guide pin is used to connect the tapered hollow reamer pilot to the reusable shaft during assembly. The cylindrical guide pin is then removed leaving behind a central hole in the assembled reamer, which may be advantageously used to guide the reamer in the bone cavity when a guide pin is inserted into the bone at a selected location This second variant of the tapered hollow assembled reamer with a removable cylindrical guide pin is most suited for cannulated application, wherein a bone cavity is already present and is commonly used for enlarging a bone cavity or removing previously used adhesive cements in a bone cavity prior to insertion of a fresh bone stem. The torque transmission between the shaft and the reamer is accomplished through one or more torque transmission tabs in the tapered end of the tapered hollow reamer engaging with one or more slots present in the tapered body element of the shaft similar to the first variant of the first embodiment discussed above.

A third variant of the first embodiment uses a guide pin with threading attachment means provided both on the distal end and on the proximal end. The guide pin distal end has a threaded male end that engages with a threaded aperture provided in the pilot potion of the tapered hollow reamer, assuring concentricity of the reamer with respect to the centerline of the shaft. The guide pin also has a threaded male member at its proximal end, which engages with corresponding threaded aperture in the tapered body element of the reusable shaft. The threads in the proximal and distal end are similar in thread orientation in that they both tighten when the shaft or guide pin is turned in the same direction. This assembly may be conveniently accomplished by turning the guide pin, first using a socket inserted through the aperture in the pilot securing the pilot of the reamer to the guide pin. Next, the shaft is turned about its axis to engage the threads of the proximal end of the guide pin with the threads within the central aperture of the shaft tapered body element until the tapered body element snugly contacts the proximal end taper of the reamer further assuring concentricity of the reamer with respect to the centerline of the shaft. Torque transmission between the shaft and the reamer is accomplished by the threaded connections between the shaft and the guide pin and between the guide pin and the reamer. This assembled reamer has the guide pin present within the reamer and thus provides additional flexural strength to the reamer and thus is useful both for non-cannulated and cannulated applications. A cannulated application requires the guide pin to have a central aperture allowing a guide pin inserted in the bone cavity or bone surface to guide the reaming direction.

The second embodiment of the invention relates to attaching a spherical hollow reamer to a reusable shaft using a special tool precisely aligning the centerline of the shaft with that of the spherical hollow reamer assisted by a guide pin. This guide pin has both distal and proximal ends threaded similar to the third variant of the first embodiment and is used to assemble a spherical hollow reamer with a reusable shaft. The shaft has a tapered body element that engages a taper present in the interior of the hollow tapered reamer during assembly ensuring concentricity of the spherical hollow reamer with respect to the centerline of the reusable shaft providing wobble-free reaming of a spherical cavity. The guide pin is not removed and provided additional rigidity to the spherical hollow reamer assembly. The threads in the distal and proximal ends are similar in thread orientation in that they both tighten when the shaft or the guide pin is turned in the same direction. This assembly may be conveniently accomplished by first turning the guide pin using a socket inserted through a central aperture of the spherical hollow reamer for engagement of the spherical hollow spherical reamer with guide pin followed by turning the shaft to engage the proximal end of the guide pin with the shaft. Torque transmission between the shaft and the reamer is accomplished by the threaded connections between the shaft and the guide pin and between the guide pin and the reamer.

The tool for assembling the first embodiment comprises a tool member with a fixed jaw in the distal end and an adjustable jaw in the proximal end, which may be moved by hand pressure application similar to a glue gun. The hollow tapered reamer with the inserted guide pin of the first and second variant of the first embodiment is placed on the fixed end of the tool member. The tapered body element central aperture of the shaft is next aligned with the protruding guide pin and one or more torque transmitting tabs are aligned with the corresponding one or more slots of the shaft tapered body element. The shaft is first pushed in manually followed by forceful displacement of the shaft into reamer until the conical taper of the interior of the reamer engages the conical taper of the tapered body element on the distal end of the shaft. At this stage, the barbell of the guide pin of the first variant of the first embodiment is seated against the pilot of the reamer. Now, the adjustable end of the tool bends the outer proximal edge of the reamer against the proximal end of the tapered body element of the shaft thereby securing the shaft against the reamer while maintaining the concentricity. In the case of the second variant of the first embodiment, the guide pin is withdrawn from the pilot exposing the central aperture within the reamer which may be used to accept a bone inserted guide pin that guides the reaming direction precisely along a pre-selected path. The assembly procedure according to third variant of the first embodiment and the second embodiment which attaches a spherical hollow reamer to a reusable shaft using a threaded connection is similar in that the guide pin is turned first using a hex nut in order to bring the guide pin within the threaded aperture of the pilot or the central aperture of the spherical reamer. Next, the shaft is turned on its axis to engage the threads of the proximal end of the guide pin with the threads in the distal end of the central aperture of the tapered body element of the shaft. At the same time, the conical taper of the tapered body element of the shaft engages the conical taper of the external surface of the tapered hollow reamer proximal of the third variant of the first embodiment or the spherical reamer of the second embodiment. In both cases, the concentricity of the reamer is maintained by the guide pin and is further assisted by the engagement of the conical taper of the reamer with the tapered body element of the shaft. The torque from the shaft is transmitted to the reamer through the two tightened threaded connections since the direction of rotation of the reamer is in the same direction as that is required for tightening the two threaded attachments.

The disassembly of the reamer is accomplished by reversing the assembly procedure using the hand tool and the used reamer is discarded since it is intended for one-time use only assuring sharp cutting teeth minimizing heat build up in the one that is being reamed.

Generally stated, the low cost easy-to-assemble reamer for medical applications comprises: (a) a disposable tapered hollow reamer or a spherical hollow reamer with a pilot permanently attached at its distal end; (b) the pilot having a central aperture for accepting a guide pin; (c) the proximal end of the tapered hollow reamer or a spherical hollow reamer provided with a tapered central aperture for accepting external taper of a tapered body element of a shaft; (d) a reusable reamer shaft having an elongated body with a distal end and a proximal end; (e) said distal end of reusable reamer shaft having a tapered body element and a central aperture for accepting a guide pin; (f) a coupling portion appointed for attachment of said reamer shaft proximal end to a drilling device; (g) a guide pin aligning the centerline of the reusable shaft and the disposable tapered or spherical hollow reamer during assembly; (h) the tapered external surface of tapered body member of reamer shaft matching a correspond taper provided in a disposable tapered hollow reamer or a disposable spherical hollow reamer, further precisely aligning the centerline of the reamer with the center line of the shaft during assembly; (i) torque transmission capability between said shaft and reamer provided by one or more tapered hollow reamer tabs engaging with matching one or more slots provided on the said tapered body element of the shaft or by having threaded attachment of the distal end of the guide pin with threads in the central aperture of the pilot and threaded attachment of proximal end of guide pin with the threads in the central aperture of the tapered body element of the shaft; (j) the bone cement debris or bone shaving produced during reaming collected within the central accumulation space of the tapered or spherical hollow reamer thereby rapidly removing bone cement debris or bone shavings from the cutting surface preventing heat build up at the bone-reamer interface.

The present invention of easily assembled modular low cost tapered or spherical hollow reamer solves the problems associated with the prior art reamers. In accordance with the present invention, the low-cost, modular tapered or spherical hollow reamer for medical applications is easily assembled and disassembled using a tool that precisely aligns the centerline of the reamer with that of the shaft during assembly, whereby the hollow reamer is attached to a reusable shaft assisted by a guide pin. Once assembled, the low cost modular tapered or spherical hollow reamer of the present invention transfers shaft torque reliably to the reamer while at the same time maintains the centerline of the reamer, preventing wobbliness thereof during cutting. Bone and bone cement fragments are collected and stored away from the bone cutting area thereby reducing the possibility of bone fragment incorporation into living bone tissue. The low cost modular tapered or spherical hollow reamer gradually crates the bone cavity due to the taper or spherical contour provided, thereby reducing heat during its surgical usage. Owing to the presence of these features, the low cost modular tapered or spherical hollow reamer of this invention is safer to use and operates more efficiently than prior art reamers.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

Reaming of the internal canal of bones is required in many surgical procedures of orthopedic surgery. These procedures include hip replacement, knee replacement and shoulder replacement. Reamers are also used in procedures that involve the internal fixation of fractures. Prior art reamers typically fall into two major classes: rigid and flexible shaft. Typically, reaming of the internal bone canal is achieved through utilization of a solid cylindrical or tapered reamer. Solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid cylindrical or tapered reamers are intended for multiple uses and therefore become less efficient after each surgery, resulting in poor cutting performance and bone necrosis. These dull blades also incorporate bone debris or bone cement debris into the living bone tissue, creating bone healing problems.

If the clinical application requires a guide pin to provide a controlled path for the cutter, it requires that the design provide a complete through hole, which passes through the assembled disposable reamer and the reusable reamer shaft. The current design provides both options through the use of a guide pin. A cannulated reamer assembly uses a guide pin first to accurately align the reamer concentric with the shaft axis and is removed provided a central hole, which may be used for accepting a bone inserted guide pin that accurately sets the reaming direction. In another version of the disposable tapered hollow reamer with a reusable shaft uses a guide pin which is left behind within the assembly thereby providing additional rigidity for the tapered hollow reamer and is extremely desirable in non-cannulated application wherein a bone cavity is drilled on a fresh bone with no previously drilled cavity.

Figure 1:
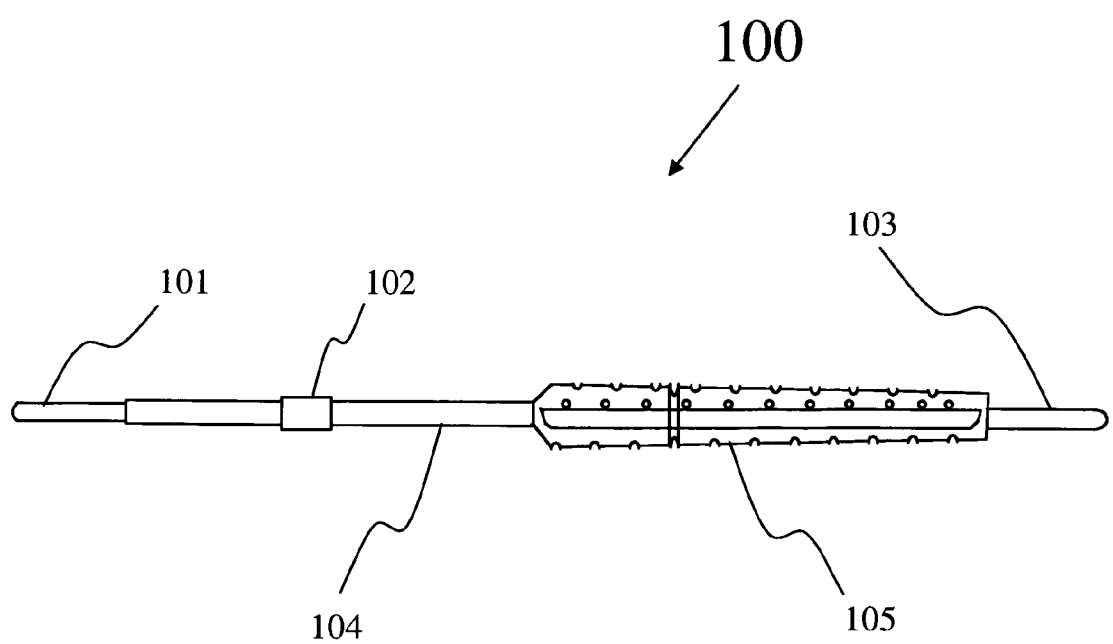
FIG. 1 is a perspective view depicting a medical tapered reamer found in the prior art.

Reaming of the internal canal of bones is required during many orthopedic surgical procedures. These procedures include hip replacement, knee replacement and shoulder replacement. Other surgical procedures that see the use of reamers include internal fixation procedures for fractures. Typically, reaming of the internal bone canal is achieved through utilization of a solid cylindrical or tapered reamer, illustrated in FIG. 1 at 100. Prior art reamers typically include a driver coupling 101 (shown as a Jacob chuck connector), a size designation 102, a pilot tip 103, a shaft 104, and cutting flutes 105. FIG. 1 shows a tapered reamer, however cylindrical reamers of similar design also exist in the prior art. Those solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. The bone or bone cement debris collected is pushed against the living bone tissue and may be incorporated into the bone. Currently utilized solid cylindrical or tapered reamers are intended for multiple uses and therefore become less efficient after each surgery, resulting in poor cutting performance and bone necrosis.

Figure 2A:
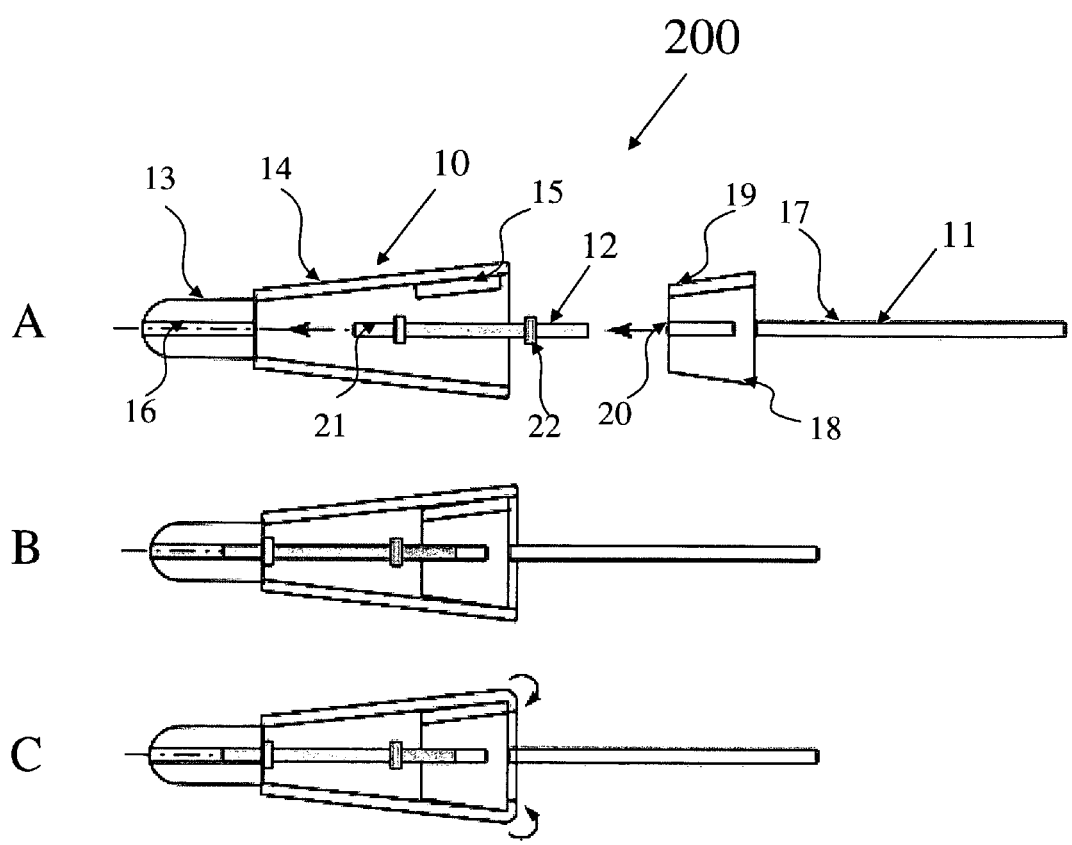
FIG. 2A shows three views, FIGS. 2A.1, 2A.2 and 2A.3, depicting assembly of a tapered hollow reamer of the subject invention according to the first variant of the first embodiment assembled on a reusable shaft.
Figure 2B:
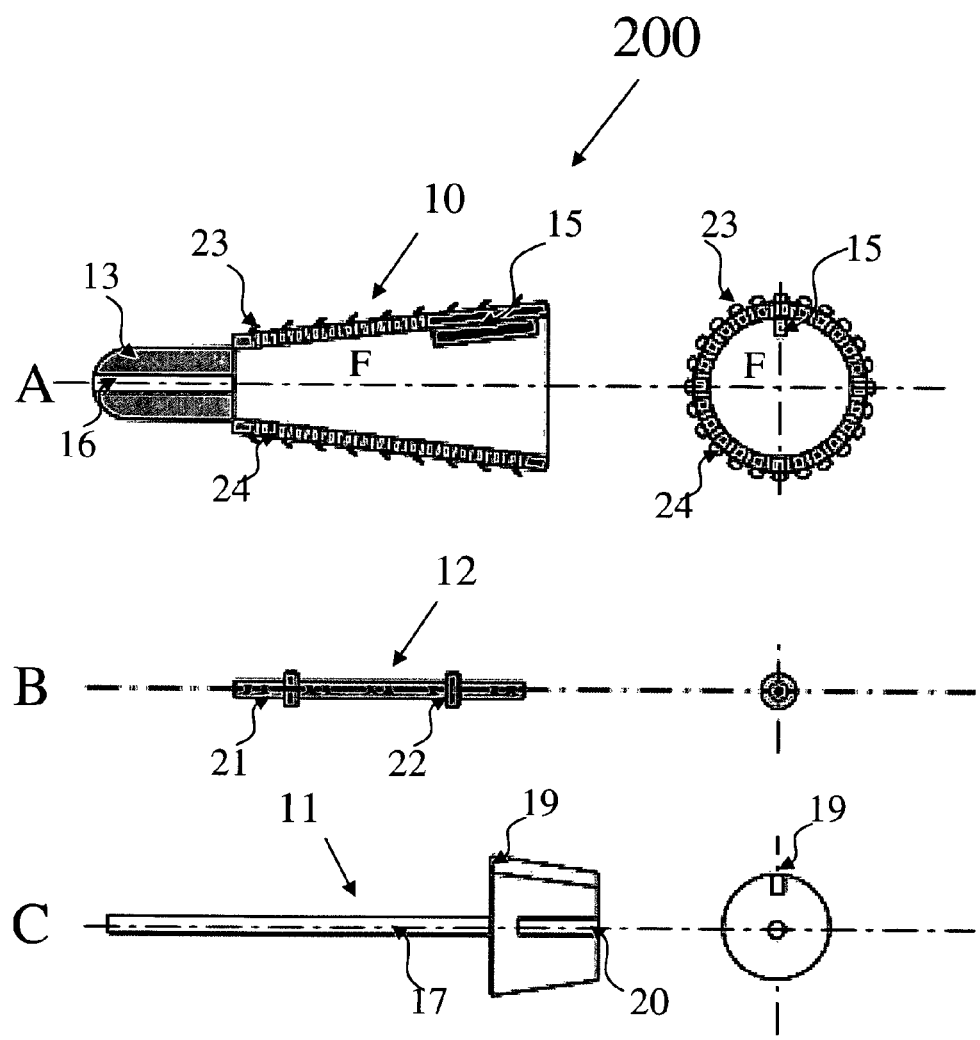
FIG. 2B shows three views, FIGS. 2B.1, 2B.2 and 2B.3, depicting details of individual components of a tapered hollow reamer of the subject invention according to the first variant of the first embodiment.

FIG. 2A depicts at 200 the low cost modular disposable tapered hollow reamer assembly of the present invention according to the first variant of the first embodiment in three views FIGS. 2A.1, 2A.2 and 2A.3. The tapered hollow reamer 10 shown at FIG. 2A.1 has a reaming portion 14, which is attached at the distal end to a pilot 13. The pilot has a central aperture 16, which accepts a guide pin that typically has a diameter of 3 mm as shown by the arrow. The proximal end of the reamer is conical in shape with an interior taper which carries a torque-transmitting tab 15. The barbell shaped guide pin 12 has a central cylindrical rod 21 typically 3.2 mm in diameter with two bar bells 22 as shown. The shaft 11 has a tapered body element 18 which has an external taper that matches the internal taper of the reamer and has a slot 19 that has the same dimension as that of the torque transmitting tab in the interior surface of the reamer. The shaft distal end tapered body element has a central aperture 20, which is also typically 3.5 mm in diameter and accepts the proximal end of the guide pin as shown by the arrow. The first stage of the assembly of the low cost disposable tapered hollow reamer according to the first variant of the first embodiment is shown at FIG. 2A.2. The distal end of the guide pin is inserted into the aperture of the pilot and the proximal end of the guide pin engages the central aperture in the tapered body element of the shaft while the conical interior surface of the reamer contacts the external taper of the tapered body element of the shaft, aligning the centerline of the reamer with that of the shaft. The torque-transmitting tab of the reamer engages the slot within the tapered body element of the shaft allowing the shaft torque to be transmitted to the reamer. The proximal end of the reamer is folded over the tapered body element of the shaft as shown at FIG. 2A.3 thereby securing the shaft within the reamer preventing its movement. While FIG. 2A illustrates one torque-transmitting tab for clarity while in practice, several torque transmitting tabs may be used. Since the guide pin 12 is captured within the reamer it provides flexural rigidity and this rigid reamer is most suited for reaming a non-cannulated bone cavity wherein no previously reamed bone cavity is present. It may also be used for connulated application. Optionally, the guide pin may be provided with a central aperture (not shown) creating a central aperture through the entire length of the assembled reamer for use in guiding reaming direction with a bone inserted guide pin. FIG. 2B shows at 200 the details of each of the components of the tapered hollow reamer in three views FIGS. 2B.1, 2B.2 and 2B.3, according to the first variant of the first embodiment of the invention illustrating both front view and side view. The cutters are shown at 23 and the aperture 24 through which the debris enters the free space F is shown.

Figure 3A:
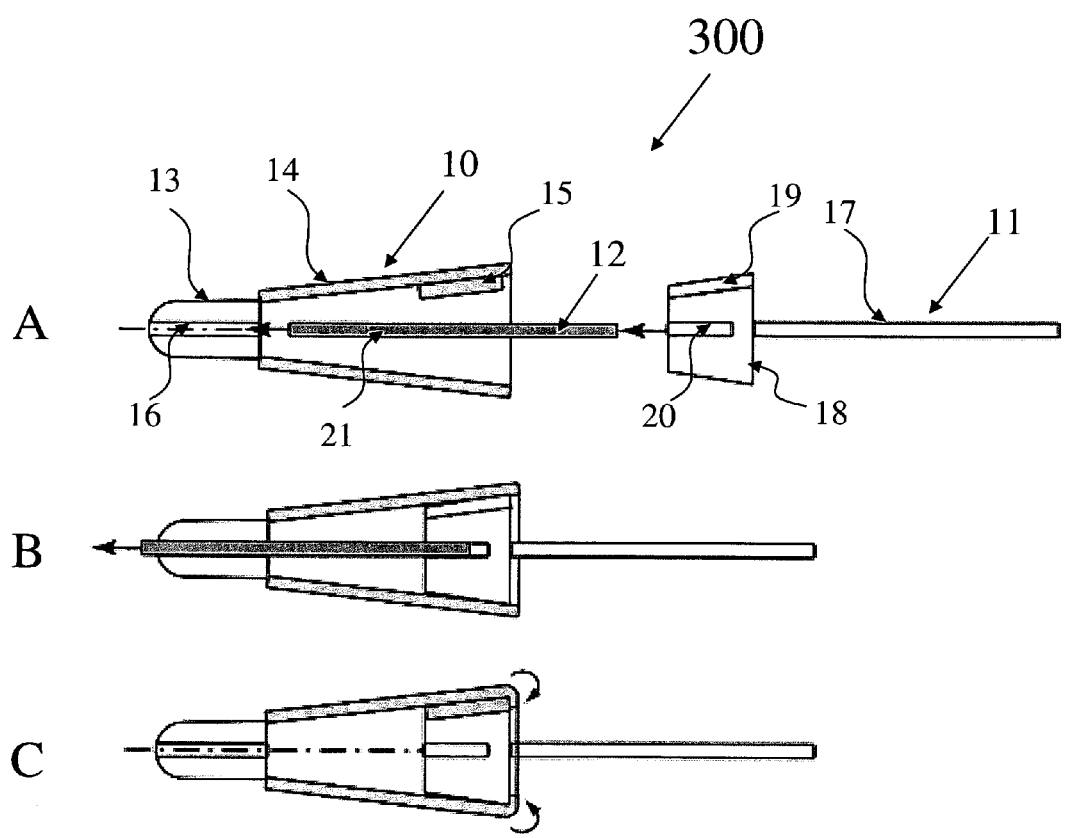
FIG. 3A shows three views, FIGS. 3A.1, 3A.2 and 3A.3 depicting assembly of a tapered hollow reamer of the subject invention according to the second variant of the first embodiment assembled on a reusable shaft.
Figure 3B:
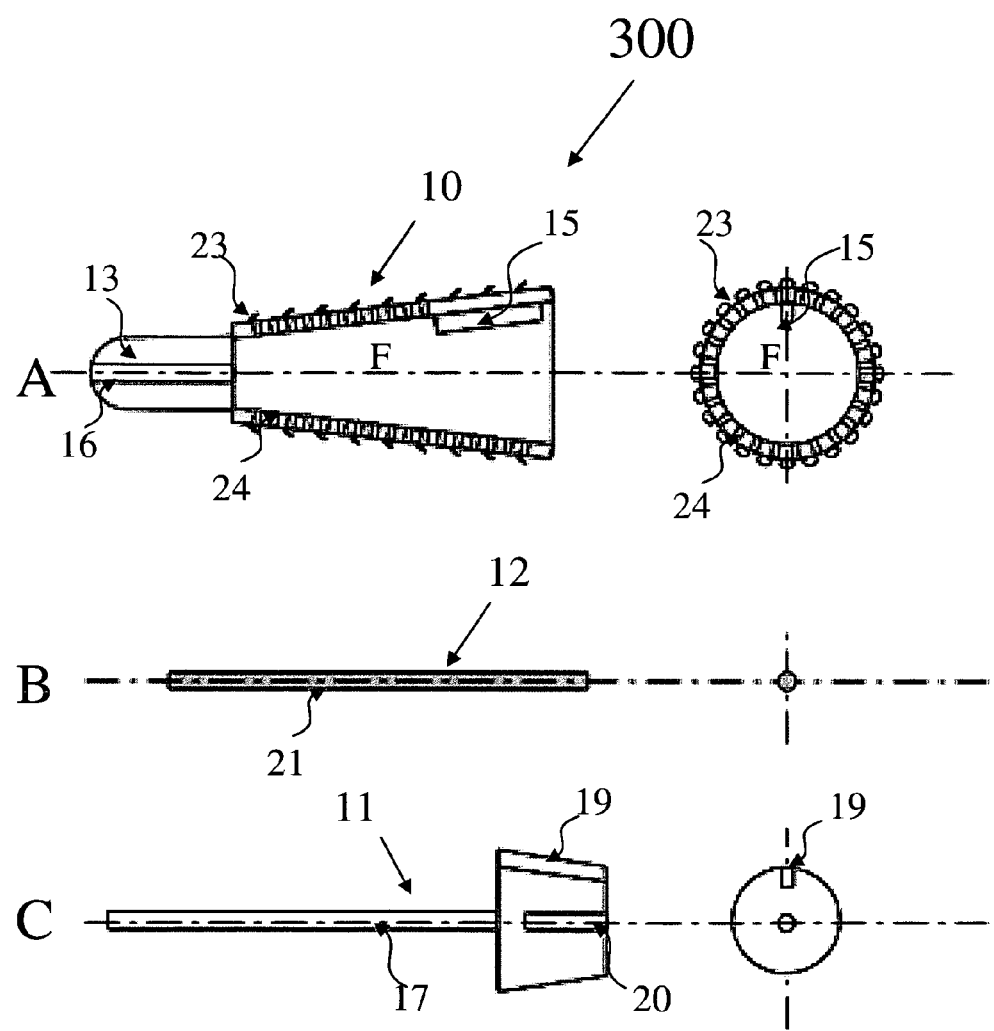
FIG. 3B shows three views FIGS. 3B.1, 3B.2 and 3B.3 depicting details of individual components of a tapered hollow reamer of the subject invention according to the second variant of the first embodiment.

FIG. 3A illustrates the second variant of the first embodiment in three views FIGS. 3A.1, 3A.2 and 3A.3, wherein the structure is similar to the first variant of the first embodiment, except that the guide pin 12 is a cylindrical guide pin but with no barbells. Identical numbering scheme is used for clarity. FIG. 3A depicts at 300 the low cost modular disposable tapered hollow reamer assembly of the present invention according to the second variant of the first embodiment. The tapered hollow reamer 10 shown at FIG. 3.A.1 has a reaming portion 14, which is attached at the distal end to a pilot 13. The pilot has a central aperture 16, which accepts a guide pin that typically has a diameter of 3 mm as shown by the arrow. The proximal end of the reamer is conical in shape with an interior taper which carries a torque-transmitting tab 15. The cylindrical guide pin 12 has a central cylindrical rod 21 typically 3 mm in diameter as shown. The shaft 11 has a tapered body element 18 which has an external taper that matches the internal taper of the reamer and has a slot 19 that has the same dimension as that of the torque transmitting tab in the interior surface of the reamer. The shaft distal end tapered body element has a central aperture 20, which is also typically 3 mm in diameter and accepts the proximal end of the guide pin as shown by the arrow. The first stage of the assembly of the low cost disposable tapered hollow reamer according to the second variant of the first embodiment is shown at FIG. 3A.2. The distal end of the guide pin is inserted into the aperture of the pilot and the proximal end of the guide pin engages the central aperture in the tapered body element of the shaft while the conical interior surface of the reamer contacts the external taper of the tapered body element of the shaft, aligning the centerline of the reamer with that of the shaft. The torque-transmitting tab of the reamer engages the slot within the tapered body element of the shaft allowing the shaft torque to be transmitted to the reamer. The proximal end of the reamer is folded over the tapered body element of the shaft as shown at FIG. 3A.3 thereby securing the shaft within the reamer preventing its movement. While FIG. 3A illustrates one torque-transmitting tab for clarity while in practice, several torque transmitting tabs may be used. The guide pin 12 is pulled away from the assembled reamer providing a central aperture in the reamer for accepting a bone inserted guide pin that sets the reaming direction precisely. This reamer is most suited for reaming a cannulated bone cavity wherein a previously reamed bone cavity is present. FIG. 3B shows the details of each of the components of the tapered hollow reamer in three views FIGS. 3B.1, 3B.2 ands 3B.3 according to the second variant of the first embodiment of the invention illustrating both front view and side views. The cutters are shown at 23 and the aperture 24 through which the debris enters into the free space F is shown.

Figure 4A:
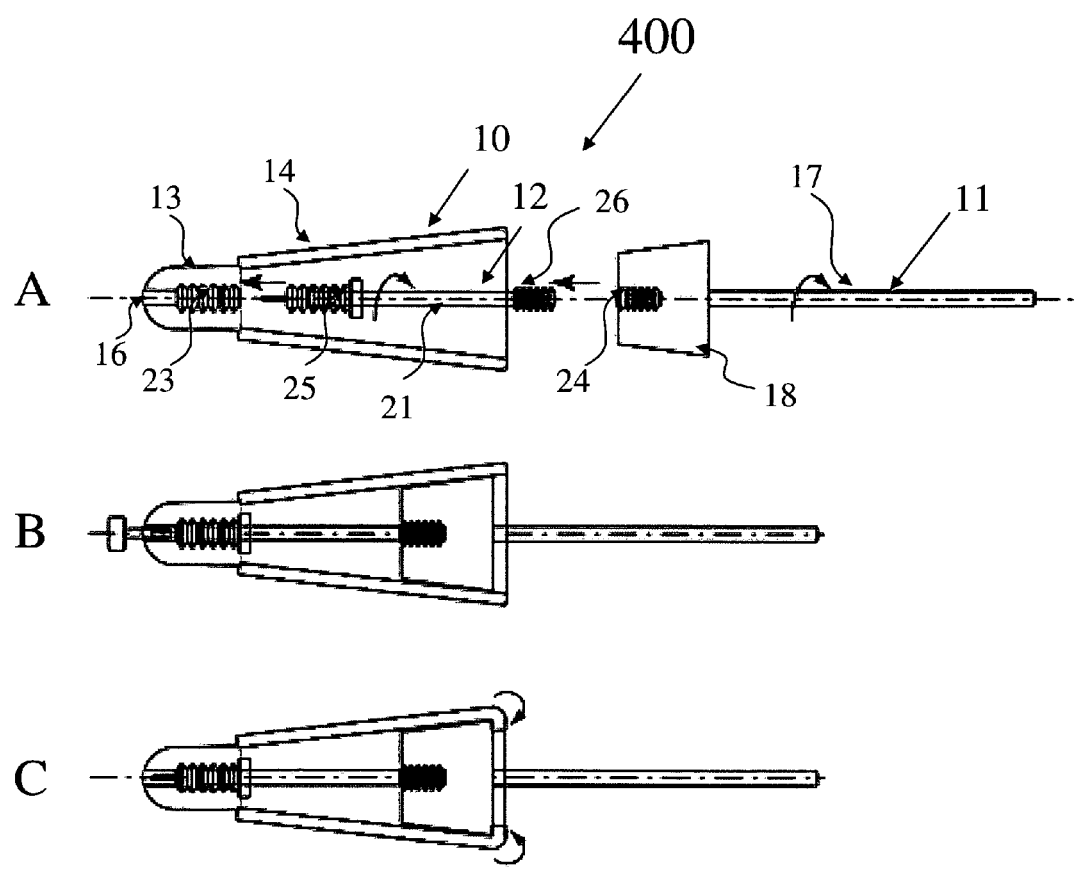
FIG. 4A shows three views FIGS. 4A.1, 4A.2 and 4A.3 depicting assembly of a tapered hollow reamer of the subject invention according to the third variant of the first embodiment assembled on a reusable shaft.
Figure 4B:
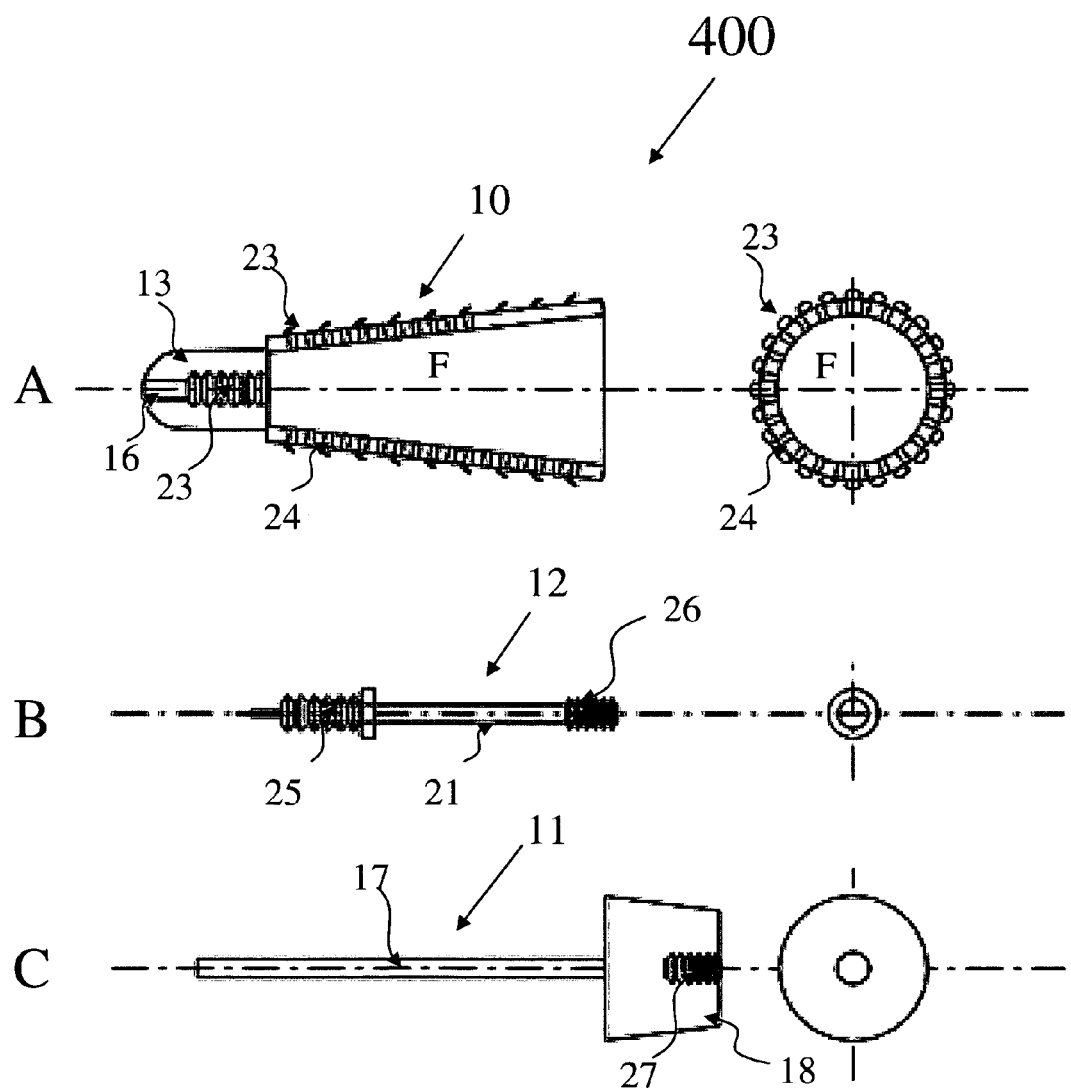
FIG. 4B shows three views FIGS. 4B.1, 4B.2 and 4B.3 depicting details of individual components of a tapered hollow reamer of the subject invention according to the third variant of the first embodiment.

FIG. 4A illustrates the third variant of the first embodiment in three views FIGS. 4A.1, 4A.2 and 4A.3 wherein the structure is similar to the first and second variants of the first embodiment, except that the guide pin 12 is a cylindrical guide pin with threads on its proximal and distal ends engaging with the pilot and tapered body element at the distal end of the shaft. Identical numbering system is used for clarity. FIG. 4A depicts at 400 the low cost modular disposable tapered hollow reamer assembly of the present invention according to the third variant of the first embodiment. The tapered hollow reamer 10 shown at FIG. 4A.1 has a reaming portion 14, which is attached at the distal end to a pilot 13. The pilot has a threaded central aperture 16, which accepts a guide pin threaded distal end that typically has a diameter of 3 mm as shown by the arrow. The proximal end of the reamer is conical in shape with an interior taper. The cylindrical shaped guide pin 12 has a central cylindrical rod 21 typically 3 mm in diameter with a threaded distal end 25 and a threaded proximal end 26 as shown. The shaft 11 has a tapered body element 18, which has an external taper that matches the internal taper of the reamer. The shaft distal end tapered body element has a threaded central aperture 20, which is also typically 3 mm in diameter and accepts the proximal end threads of the guide pin as shown by the arrow. The first stage of the assembly of the low cost disposable tapered hollow reamer according to the third variant of the first embodiment is shown at FIG. 4A.2. The distal end threads 23 of the guide pin is inserted into the aperture of the pilot and the guide pin is turned using a hex socket 25 to secure the guide pin 12 to the pilot 13. Next, the shaft 11 is turned to engage the proximal end threads 24 of the guide pin with the threads 20 of the central aperture in the tapered body element of the shaft while the conical interior surface of the reamer contacts the external taper of the tapered body element of the shaft, aligning the centerline of the reamer with that of the shaft. The threaded attachment allows the shaft torque to be transmitted to the reamer. The proximal end of the reamer is folded over the tapered body element of the shaft as shown at FIG. 4A.3 thereby securing the shaft within the reamer preventing its movement. Since the guide pin 12 is captured within the reamer it provides flexural rigidity and this rigid reamer is most suited for reaming a non-cannulated bone cavity wherein no previously reamed bone cavity is present. It may also be used for connulated application. Optionally, the guide pin may be provided with a central aperture (not shown) creating a central aperture through the entire length of the assembled reamer for use in guiding reaming direction with a bone inserted guide pin. FIG. 4B shows the details of each of the components of the tapered hollow reamer in three views FIGS. 4B.1, 43B.2 and 4B.3 according to the third variant of the first embodiment of the invention illustrating both front view and side view. The root diameter of the threads in the pilot 13 and tapered body element 18 is typically 3.2 mm. The cutters are shown at 23 and the aperture through which the debris enters the free space F is shown at 24.

A number of sizes of tapered hollow reamers are available along with their shafts and modular pilots so that the surgeon can choose progressively larger hollow tapered reamers for a fresh bone canal or a reworked bone canal. Since the low cost tapered hollow reamer 10 is disposable, the cutting performance of the hollow reamer is not compromised through repeated use. Several limitations of the prior art reamers and consequent clinical problems seen are overcome through utilization of the disposable modular tapered hollow reamers herein. Novel design features of the hollow reamers of the present invention and improvements to prior art reamers are multifaceted. Moreover, when dealing with revision hip surgery, the hollow reamers have also been designed to cut bone cement (PMMA) in a more efficient manner by providing internal space within the low cost tapered hollow reamer to capture the debris. This feature reduces both the cutting temperature and time required to remove the remnant cement mantle. The bone debris collected may be used for bone grafting or other specific surgical procedures. A further advantage of the hollow design is that by allowing the removal of the bone debris from the outer surface of the reamer to the inside of the reamer, the reamer is less likely to raise the intramedulary pressure in the long bone being reamed, thereby lessening the chance of fat embolism during these procedures.

Figure 5A:
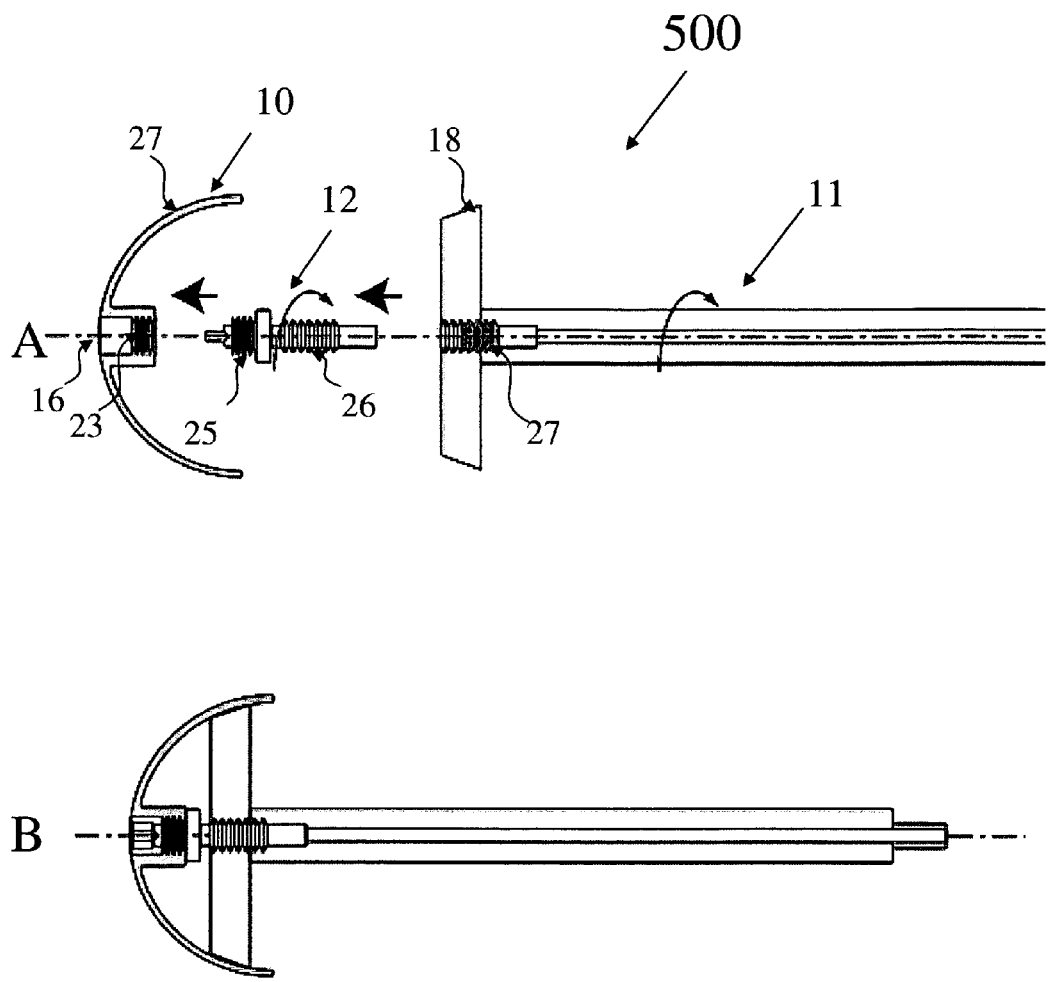
FIG. 5A shows two views FIGS. 5A.1 and 5A.2 depicting assembly of a spherical hollow reamer of the subject invention according to the second embodiment assembled on a reusable shaft.
Figure 5B:
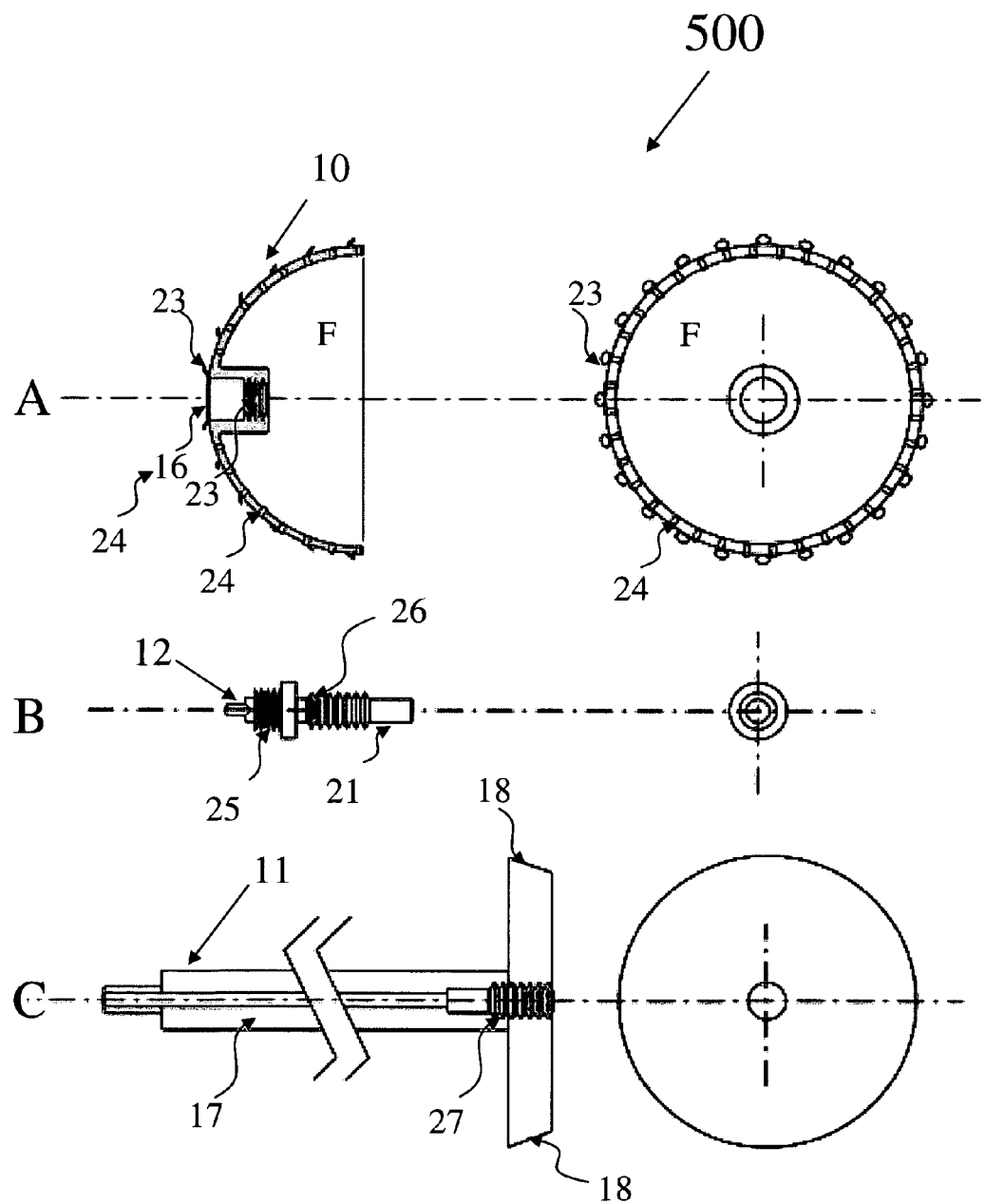
FIG. 5B shows three views FIGS. 5B.1, 5B.2 and 5B.3 depicting details of individual components of a spherical hollow reamer of the subject invention according to the second embodiment.

FIG. 5A illustrates in two views FIGS. 5A.1 and 5A.2 the second embodiment of the invention wherein a disposable spherical reamer is attached to a reusable shaft using a threaded connection similar to the third variant of the first embodiment. The guide pin 12 is a cylindrical guide pin with threads 23 distal end and threads 24 on its proximal end engaging with threads 16 in the central aperture of the spherical hollow reamer and threads 20 in the central aperture of the tapered body element at the distal end of the shaft. Identical numbering system is used for clarity. FIG. 5A depicts at 500 the low cost modular disposable spherical hollow reamer assembly of the present invention according to the second embodiment. The spherical hollow reamer 10 shown at FIG. 5A.1 has a reaming portion 29. The central portion of the spherical reamer has central aperture large enough to accept a hex nut for tightening the guide pin and has a threaded central aperture 16. The threaded aperture 16 accepts threaded distal end 23 of a guide pin as shown by the arrow. The threads typically have a root diameter of 3.2 mm. The proximal end of the spherical reamer has a conical interior taper. The cylindrical shaped guide pin 12 has a central cylindrical rod 21 a threaded distal end 23 and a threaded proximal end 24 as shown. The shaft 11 has a tapered body element 18, which has an external taper that matches the internal taper of the proximal end of the spherical reamer. The shaft distal end tapered body element has a threaded central aperture 20, which is also typically 3 mm in diameter and accepts the proximal end threads 24 of the guide pin as shown by the arrow. The assembly of the low cost disposable spherical hollow reamer according to the second embodiment is shown at FIG. 5A.2. The distal end of the guide pin is inserted into the aperture of the central aperture of the spherical hollow reamer and the guide pin is turned using a hex socket similar to FIG. 4A.2 (not shown) to secure the guide pin 12 to the pilot 13. Next, the shaft is turned to engage the proximal end threads 24 of the guide pin with the threads 20 of the central aperture in the tapered body element of the shaft while the conical interior surface of the spherical hollow reamer contacts the external taper of the tapered body element of the shaft, aligning the centerline of the reamer with that of the shaft. The threaded attachment allows the shaft torque to be transmitted to the reamer. Since the guide pin 12 is captured within the reamer it provides flexural rigidity and this rigid reamer is most suited for reaming a non-cannulated bone cavity wherein no previously reamed bone cavity is present. It may also be used for cannulated application. FIG. 5B shows in three views FIGS. 5B.1, 5B.2 and 5B.3, the details of each of the components of the spherical hollow reamer according to the second embodiment of the invention illustrating both the front view and the side view. The root diameter of the central threads 16 of the spherical hollow reamer and threads 20 of the tapered body element 18 are typically 3.2 mm. The cutters are shown at 23 and the aperture through which the debris enters the free space F is shown at 24.

A number of sizes of spherical hollow reamers are available along with their shafts so that the surgeon can choose progressively larger spherical hollow reamers for a fresh bone acetabular cavity or a reworked bone acetabular cavity. Since the low cost spherical hollow reamer 10 is disposable, the cutting performance of the spherical hollow reamer is not compromised through repeated use. Several limitations of the prior art reamers and consequent clinical problems seen are overcome through utilization of the disposable modular tapered hollow reamers herein. Novel design features of the spherical hollow reamers of the present invention and improvements to prior art reamers are multifaceted. Moreover, when dealing with revision surgery, the spherical hollow reamers have also been designed to cut bone cement (PMMA) in a more efficient manner by providing internal space within the low cost tapered hollow reamer to capture the debris. This feature reduces both the cutting temperature and time required to remove the remnant cement mantle. The bone debris collected may be used for bone grafting or other specific surgical procedures. A further advantage of the hollow design is that by allowing the removal of the bone debris from the outer surface of the reamer to the inside of the reamer, the reamer is less likely to raise the intramedulary pressure in the long bone being reamed, thereby lessening the chance of fat embolism during these procedures.

Figure 6:
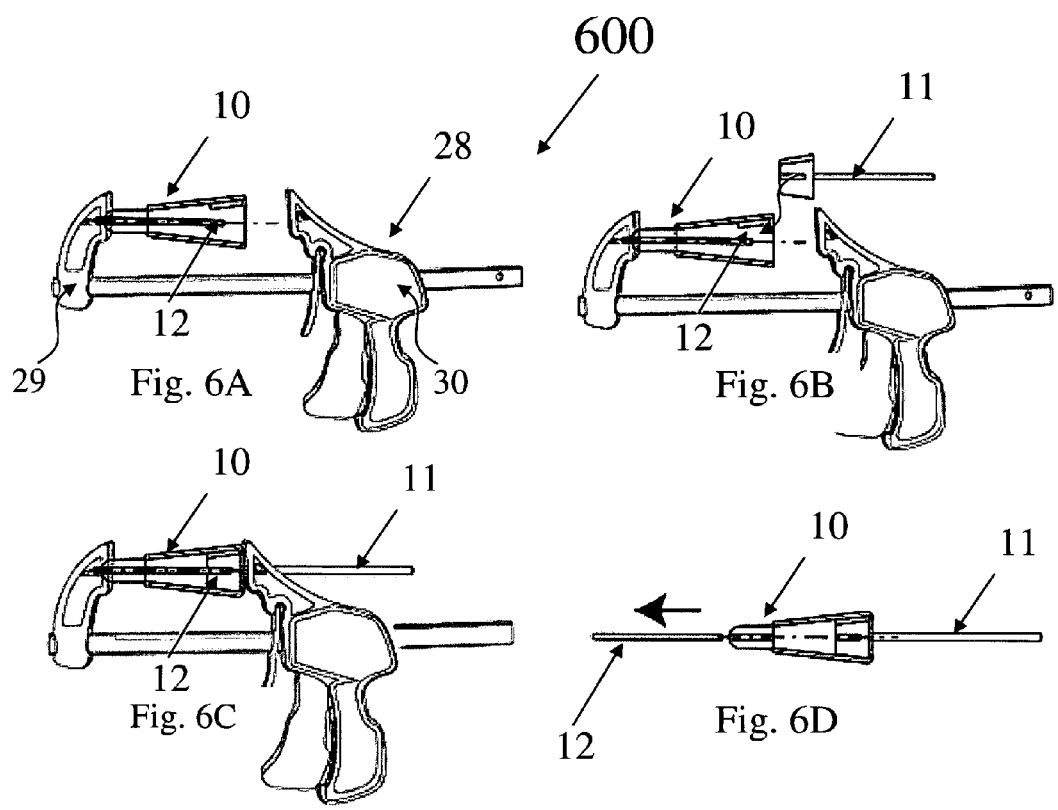
FIG. 6 depicts in four views FIGS. 6A, 6B, 6C and 6D a perspective view of the assembly of a tapered hollow reamer according to the second variant of the first embodiment of the invention using a hand tool.

FIG. 6 depicts at 600 four views FIGS. 6A, 6B, 6C and 6D of a perspective view of the assembly of a tapered hollow reamer according to the second variant of the first embodiment of the invention using a hand tool. The hand tool 28 is similar to a glue gun and has a fixed portion 29 and an adjustable portion 30. The reamer 10 of the second variant of the first embodiment with the cylindrical guide pin placed within the central aperture of the pilot is placed on the fixed portion 29 of the hand tool 28 as shown in FIG. 6A. Now the shaft 11 is brought in and inserted within the taper of the proximal end of the reamer engaging the protruding guide pin, torque transmitting tab and hand pushed along the direction of the arrow as shown in FIG. 6B. The adjustable portion 30 of the hand tool 28 is then brought to apply pressure to the tapered body element of the shaft 11 and deform or bend the proximal ends of the reamer 10 as shown in FIG. 6C. The assembled reamer is removed from the hand tool and the guide pin 12 is slid off from the pilot portion of the assembled reamer as shown in FIG. 6D exposing a central hole within the assembled reamer which may be used to guide the reamer in a direction set by a bone inserted guide pin.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A modular tapered hollow reamer for medical applications, comprising:
   a. a shaft portion having an elongated body with a proximal end and a distal end, said proximal end having a coupling portion appointed for attachment of said reamer to a drilling device, said distal end having a tapered body element with a central aperture, external surface taper and one or more torque transmitting slots on said external surface taper;
   b. a disposable tapered hollow reamer portion, comprising:
      1. a hollow reamer having permanently attached pilot with a central aperture extending therethrough and terminating at a central hole in the distal end, a tapered central hollow reamer portion and a tapered interior aperture in the proximal end with a taper angle matching said external surface taper of said tapered body element of said shaft;
      2. a plurality of externally protruding cutters, and a plurality of apertures extending through the thickness of said tapered reamer between the distal end and the proximal end;
   c. a removable guide pin having a distal end, central portion and proximal end and said distal end and proximal end provided with attachment means for securing said guide pin to the central aperture of said tapered body element of the shaft and said central apertures of said disposable tapered hollow reamer;
   whereby the reamer assembly transmits torque from the shaft to said disposable tapered hollow reamer through torque transmitting tabs and slots and;
   guide pin insertion and contact between the external surface taper of said tapered, body element of said shaft and the tapered interior aperture of said reamer ensure, during assembly, substantial coincidence of centerlines, preventing reamer wobbliness, and bone and bone cement debris is collected in the space within the tapered hollow reamer portion.

2. A modular tapered hollow reamer for medical applications as recited by claim 1, wherein said reamer assembly is assembled by a hand tool that aligns said shaft portion and said disposable hollow reamer portion assisted by said guide pin, and the proximal end of the reamer is bent over said tapered body element of the shaft, securing the shaft within the reamer.

3. A modular tapered hollow reamer for medical applications as recited by claim 1, wherein said guide pin is cylindrical with barbell shapes adjacent to the distal and proximal ends, and remains within said reamer assembly.

4. A modular tapered hollow reamer for medical applications as recited by claim 3, wherein said reamer assembly is used for reaming anon-cannulated bone cavity.

5. A modular tapered hollow reamer for medical applications as recited by claim 1, wherein said guide pin is cylindrical and is removable from said reamer assembly through said central aperture and said central hole, and wherein a bone insert guide pin is adapted to be received through said central hole of said central aperture to guide reaming direction along a pre-selected path.

6. A modular tapered hollow reamer for medical applications as recited by claim 5, wherein said reamer assembly is used for reaming a cannulated bone cavity.

7. A modular tapered hollow reamer for medical applications as recited by claim 5, wherein said central aperture within the assembled reamer is used for accepting a bone inserted guide pin, precisely setting the reaming direction of the reamer.

8. A modular tapered hollow reamer for medical applications as recited by claim 1, wherein said guide pin attachment means for securing said guide pin to the central aperture of said tapered body element of the shaft and said central aperture of the disposable tapered hollow reamer achieves a close fit between the cylindrical guide pin ends, engaging respective cylindrical apertures.

9. A modular tapered hollow reamer for medical applications as recited by claim 1, wherein said disposable tapered hollow cutter is appointed for a single, one-time use.

10. A modular tapered hollow reamer for medical applications as recited by claim 1, wherein said shaft portion is rigid.

11. A modular tapered hollow reamer for medical applications as recited by claim 1, wherein said shaft portion is flexible.

* * * * *